(12) United States Patent
Risbud et al.

(10) Patent No.: US 7,211,271 B2
(45) Date of Patent: May 1, 2007

(54) METHOD TO IMPROVE HYDROXYAPATITE IMPLANTATION AND STIMULATE BONE REGENERATION

(75) Inventors: Subhash H. Risbud, Davis, CA (US); Nancy E. Rashid, Davis, CA (US); A. Hari Reddi, El Macero, CA (US)

(73) Assignee: The Regents of the University of California, Oakland, CA (US)

( * ) Notice: Subject to any disclaimer, the term of this patent is extended or adjusted under 35 U.S.C. 154(b) by 296 days.

(21) Appl. No.: 10/150,752

(22) Filed: May 17, 2002

(65) Prior Publication Data

US 2002/0197297 A1 Dec. 26, 2002

Related U.S. Application Data

(63) Continuation-in-part of application No. 09/808,721, filed on Mar. 12, 2001, now abandoned.

(51) Int. Cl.
*A61F 2/00* (2006.01)
*A61K 38/00* (2006.01)
*C07K 17/14* (2006.01)

(52) U.S. Cl. .......................... 424/423; 514/2; 530/811

(58) Field of Classification Search ................ 424/423, 424/426, 93.7, 184, 178, 179, 180; 435/184, 435/178, 179, 180
See application file for complete search history.

(56) References Cited

U.S. PATENT DOCUMENTS

| 4,596,574 | A | 6/1986 | Urist |
| 4,681,763 | A | 7/1987 | Nathanson et al. |
| 4,774,322 | A | 9/1988 | Seyedin et al. |
| 5,158,934 | A | 10/1992 | Ammann et al. |
| 5,422,340 | A | 6/1995 | Ammann et al. |
| 5,492,697 | A | 2/1996 | Boyan et al. |
| 5,942,496 | A * | 8/1999 | Bonadio et al. ............... 514/44 |
| 6,048,964 | A | 4/2000 | Lee et al. |
| 6,143,036 | A | 11/2000 | Comfort |
| 6,302,913 | B1 * | 10/2001 | Ripamonti et al. ...... 623/16.11 |

FOREIGN PATENT DOCUMENTS

EP 0200341 A1 12/1988
EP 0169016 B1 10/1995

OTHER PUBLICATIONS

Habelitz et al., "Nitrogen-containing apatite," *Journal of the European Ceramic Society* (1999) 19: 2685-2694.
Hench, "Bioceramics," *J. Am Ceram. Soc.* (1998) 81(7): 1705-28.
Magruder et al., "Photosensitivity of B, Si and N implanted silica," *Nuclear Instruments and Methods in Physics Research* (1997) B(127/128): 492-496.
McHargue, "The effects of ion implantation on the structure of ceramics," *JOM* (Jul. 1991) 40-44.
Torrisi, "Nitridation processes of titanium for biomedical protheses," *Metallurgical Science and Technology* (1999) 17(1):27-32.
Zeng et al., "Analysis of bovine serum albumin adsorption on calcium phosphate and titanium surfaces," *Biomaterials* (1999) 20: 377-384.

* cited by examiner

*Primary Examiner*—David M. Naff
(74) *Attorney, Agent, or Firm*—Townsend and Townsend and Crew LLP.; Henry Heines

(57) ABSTRACT

Hydroxyapatite is treated by a combination of nitridation and the application of bone morphogenetic protein or DNA encoding such a protein to improve the tissue compatibility and affinity of the hydroxyapatite, rendering the hydroxyapatite more useful as a material for biomedical implants.

10 Claims, 1 Drawing Sheet

METHOD TO IMPROVE HYDROXYAPATITE IMPLANTATION AND STIMULATE BONE REGENERATION

CROSS REFERENCE TO RELATED APPLICATION

This application is a continuation-in-part of application Ser. No. 09/808,721, filed Mar. 12, 2001 now abandoned, the contents of which are incorporated herein in their entirety.

STATEMENT AS TO RIGHTS TO INVENTIONS MADE UNDER FEDERALLY SPONSORED RESEARCH AND DEVELOPMENT

This invention was made with Government support under Grant No. DMR 97-30019, awarded by the National Science Foundation. The Government has certain rights in this invention.

BACKGROUND OF THE INVENTION

1. Field of the Invention

This invention relates to biomedical and orthopedic implants and prostheses and to their use of hydroxyapatite.

2. Description of the Prior Art

Implants and prostheses are commonly used in the medical profession to replace or reinforce diseased or injured hard tissues that are either fractured, damaged, or degenerated. These devices and materials are used, for example, as heart valve replacements, hip implant stems or anchorages, dental implants, knee prostheses, and vertebral spacers. Implants are also used as bone graft substitutes, as alignment maintenance devices in spinal fusion procedures, and as reinforcements for bone weakened by tumor metastases. In some cases, the implants are organs or sections of bone that are transplanted from other portions of the patient's body, while in others, synthetic bones or organs are used. For rigid parts such as bone, fixation is typically achieved by screws, cement, or both. Softer organ and tissue implants are secured by stitching the implants to the surrounding tissues with thread. Still other implants such as breast implants and pacemakers are not securely fixed, but instead rely on natural tissue formation around the implant for securement. In all cases, the success of the implant often depends on its compatibility with, and incorporation into, the biological system, and for those intended for harder tissue, the ability of the implant to form a secure bond to the neighboring healthy tissue. The surface properties of the implant are of primary importance in achieving these goals.

Synthetic materials when used as implants offer certain advantages over transplanted materials in certain applications of this invention. In bone grafts, for instance, the use of a synthetic material rather than a portion of the patient's own iliac crest offers a lower morbidity rate at the donor site and a further advantage for growing children, who have less native bone stock available for use. In spinal fusions, synthetic hydroxyapatite offers an advantage over hydroxyapatite formed by heating coral, since synthetic hydroxyapatite can be manufactured in a less porous and hence stronger form. In cancer patients, bones that have become weakened by tumor metastasis can be replaced or reinforced by a bone graft of synthetic material, again avoiding the need for native bone stock. In other applications of the invention, porosity is desirable. These applications are those where ingrowth of blood vessels and soft tissue are desirable, i.e., those in which the implant is intended to function in a manner comparable to natural bone.

A synthetic material that demonstrates a high level of compatibility with bone and other hard tissue as well as stability in the physiological environment is hydroxyapatite. Hydroxyapatite is a calcium phosphate with the same elemental components as natural bone. Hydroxyapatite is in fact the primary mineral constituent of mammalian bone, constituting 43% by weight of bone composition. The synthetic hydroxyapatite that is used for implants differs from natural bone hydroxyapatite by having fewer impurities and a higher degree of crystallization. Some of the impurities occur as substitutions in the crystal structure. The calcium ions, for example, may be substituted by sodium, potassium, magnesium, lead, manganese, cadmium, strontium, or zinc ions; the hydroxyl sites by halide, oxygen, carbonate, and water; and the phosphate ions by arsenate, sulfate, and carbonate. Deviations from the hydroxyapatite crystal structure form further impurities. These deviations are introduced during synthesis since calcium phosphates can assume many forms and a pure hydroxyapatite material is difficult to synthesize based on the stoichiometric composition. Even though hydroxyapatite is the only calcium phosphate that is stable under normal physiological conditions and other calcium phosphate phases tend to convert to the more stable hydroxyapatite, the transition occurs slowly, allowing the less stable calcium phosphate phases to resorb into the surrounding tissue at rates that vary with their porosity and composition.

Unstable calcium phosphate phases also tend to degenerate into grains which, when released into the body, induce adverse metabolic responses such as a foreign body giant cell response or encapsulation in fibrous tissue. Small particles can also induce an immune response and at times a massive phagocytic cell response. The latter can cause the displacement of normal tissue with a weak, structureless mass of inflamed tissue, leading to the loosening of the implant. Cells that resorb damaged bone (osteoclasts) and those that rebuild bone (osteoblasts) are also affected by the release of small implant particles as the implant deteriorates: small particles tend to activate the osteoclasts and decrease the population of the osteoblasts, the net result being a loss of bone mass.

Other shortcomings of synthetic hydroxyapatite are its flexural strength, strain-to-failure ratio, and fracture toughness, all of which are low relative to bone. Synthetic hydroxyapatite is thus relatively brittle and has low fatigue resistance, and for these reasons is not used in load-bearing locations.

Various methods have been used in the prior art for modifying hydroxyapatite and other implant materials to improve their bone adhesion and other properties. Among these methods are the use of bone morphogenetic proteins as a coating on the implant surface to improve cell adhesion and subsequent tissue attachment. Methods of applying these coatings and their effects are reported in references cited by Zeng, H., et al., *Biomaterials* 20 (1999): 377–384. To improve the hardness of the implant material and its chemical inertia to the biological environment, nitrogen atoms have been introduced into the material by nitridation. This has been reported for both hydroxyapatite and titanium implants by Habelitz, S., et al., *J. European Ceramic Society* 19 (1999): 2685–2694, and Torrisi, L., *Metallurgical Science and Technology* 17(1) (1999): 27–32.

SUMMARY OF THE INVENTION

It has now been discovered that hydroxyapatite, upon receiving the combined treatment of nitridation and a bone morphogenetic protein or an analog thereof, or DNA encoding such a protein or analog, is unexpectedly favorable to tissue growth of the contacting tissue, with the two treatments displaying a synergistic effect. As a result, the affinity of a hydroxyapatite component or a hydroxyapatite-coated component of a biomedical implant for native bone or tissue is increased, the result being greater than the sum of the effects of either nitridation or treatment with the protein alone. In some cases, in fact, the nitridation when applied alone actually lessens the affinity of the surface to the adjacent tissue. Thus, it is particularly surprising that the combined treatment has such a beneficial effect.

The present invention thus resides in a method of improving hydroxyapatite-containing biomedical implants by applying the two treatments in combination. The invention also resides in novel biomedical implant materials that include either a hydroxyapatite component or coating that has undergone the combination treatment. The invention further resides in various surgical methods that involve the placement or implantation of hydroxyapatite materials in the human or mammalian body, the performance of the materials being improved by having been subjected to the combination treatment prior to implantation. These procedures and methods are discussed in more detail below.

DETAILED DESCRIPTION OF THE INVENTION AND SPECIFIC EMBODIMENTS

Figure 1:
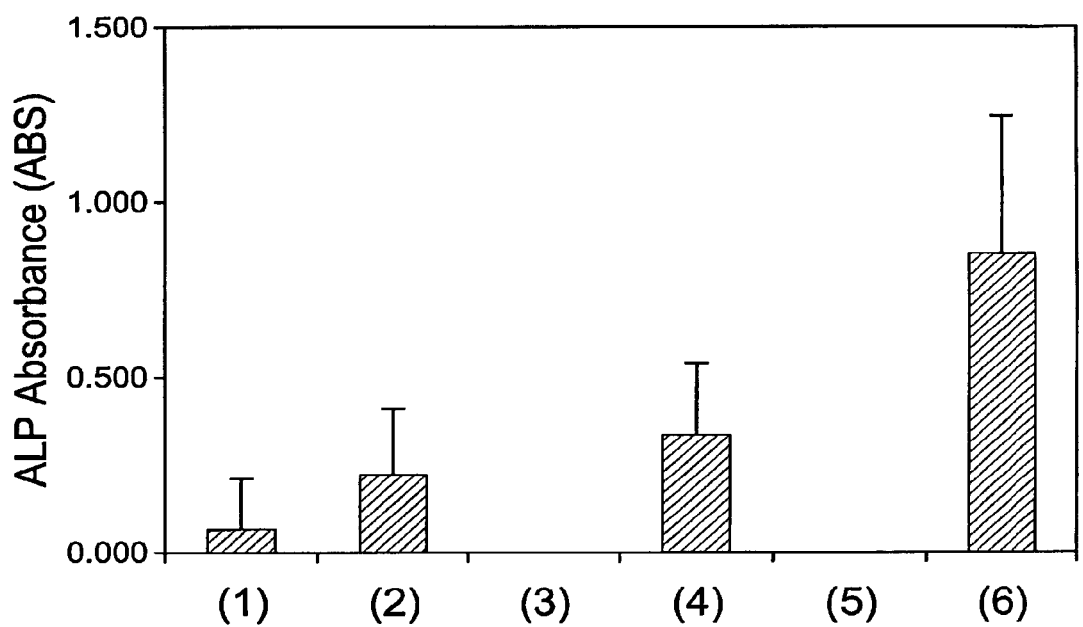
FIG. 1 is a bar graph showing the results of a series of comparisons to demonstrate the synergistic effect of the combination treatment of the present invention.

Bone morphogenetic proteins (BMPs) are members of a family of structurally and functionally related morphogenetic proteins that belong to the Transforming Growth Factor-Beta (TGF-$\beta$) superfamily. At least fifteen BMPs have been identified to date, and they are numbered consecutively, i.e., "BMP-1," "BMP-2," etc. Originally identified as protein regulators of cartilage and bone formation, BMPs have also been shown to regulate the growth, differentiation, chemotaxis, and apoptosis of various cell types, including mesenchymal cells, epithelial cells, hematopoietic cells, and neuronal cells. The BMPs have molecular weights of approximately 25 kD and are expressed as secretory polypeptide precursors that share a highly conserved bioactive cysteine domain located near their C-termini. The C-terminal domains of BMP-3, BMP-5, BMP-6, and BMP-7 (also known as OP-1 or "osteogenic protein-1") are about 60% identical to that of BMP-2, and the C-terminal domains of BMP-6 and BMP-7 are 87% identical. The BMPs also share a propensity to form homo- and heterodimers. The BMPs are highly conserved across species as well. At the amino acid sequence level, for example, mature human and mouse BMP-4 are 98% and 100% identical, respectively, to mature rat BMP-4, mature human and mouse BMP-5 are 97% identical, mature human and mouse BMP-6 are 96% identical, and mature human, mouse and rat BMP-2 are 100% identical. BMPs of particular interest in the practice of this invention are BMP-2, BMP-3, BMP-4, BMP-5, BMP-6, and BMP-7. BMP-4, BMP-6, and BMP-7 are particularly preferred.

BMPs have been isolated from biological sources using purification techniques coupled with bioassays. BMPs have also been isolated and cloned by virtue of DNA sequence homologies within conserved regions that are common to the BMP family. Synthetic BMPs and recombinant BMPs have also been prepared. A disclosure of one method of isolating BMPs from bone tissue is Urist, M. R., U.S. Pat. No. 4,294,753, issued Oct. 13, 1981, and incorporated herein by reference.

Transforming Growth Factor-Beta 1 ("TGF-$\beta$1") is a close structural analog of the BMPs. The various TGF-$\beta$s are dimers containing two identical polypeptide chains, each dimer having a molecular mass of about 25 kD. The TGF-$\beta$s, including TGF-$\beta$1, can be isolated from mammalian species in general and from bone, platelets, or placenta, and purified for use in recombinant cell culture. Methods of isolating and purifying these proteins are reported in the literature, such as for example European Patent Application No. 200 341, published Dec. 10, 1986, European Patent Application No. 169 016, published Jan. 22, 1986, and U.S. Pat. No. 4,774,322, issued Sep. 27, 1988. The contents of each of these documents are incorporated herein by reference.

The inclusion of the bone morphogenetic protein or analog in the treatment of the hydroxyapatite is achieved by applying to the hydroxyapatite either the protein itself or DNA that encodes the protein. The DNA can be supplied in any form that is known to be capable of transforming mammalian cells upon contact and expression in the cells thus transformed. If DNA is applied, a high level of expression can be obtained by subcloning the DNA into an expression vector that contains a strong promoter to direct transcription, a transcription unit or expression cassette, a transcription/translation terminator, and a ribosome-binding site for translational initiation. Bacterial expression systems and eukaryotic expression systems are well known in the art and commercially available. The transcription unit or expression cassette contains the elements required for the expression of the DNA in a host cell, which typically include a promoter linked to the nucleic acid sequence, signals for the efficient polyadenylation of the transcript, ribosome binding sites, and translation termination, and if desired, enhancers and introns. Preferred expression vectors are plasmids, and preferred plasmids for the practice of the present invention are those for BMP-4 and BMP-7, both of which are known.

Methods for direct application of either the protein or its encoding DNA are known and will be readily apparent to those skilled in the art. A common method is the simple deposition of the protein or the DNA or an appropriate vector containing the DNA from a liquid solution.

Nitridation processes are likewise disclosed in the literature, and include the use of dry ammonia, aqueous ammonia, and nitrogen monoxide. Gaseous molecular nitrogen can be ionized by the action of electrical discharges to form an ionic plasma. Thermal nitridation with nitrogen-containing gas is another option, whereby the hydroxyapatite is placed with the gas in a heated chamber at temperatures between 300° C. and 1100° C. These and other nitridation methods are disclosed for example by Habelitz et al. and Torrisi, referenced above. The degree of nitridation is not critical to the invention and may vary. In most applications, best results will be obtained with nitridation within the range of about 1% by weight to about 4% by weight. In the preferred practice of this invention, the nitridation is performed prior to the protein treatment.

Hydroxyapatite is a crystal form of calcium phosphate having the empirical formula $Ca_{10}(PO_4)_6(OH)_2$. Dense hydroxyapatite is made by compressing calcium phosphate solids from a very fine powder into a pellet which is then heat treated to fuse the powder particles together. A disclosure of this process is provided by Jarcho, M., *J. Mater. Sci.* 11: 2027 (1976).

Hydroxyapatite that has been treated in accordance with this invention can be used as components or coatings for dental implants, knee prostheses, vertebral spacers, hip implants, heart valve replacements, and any of a variety of other orthopedic or biomedical implants that would benefit from an improved affinity to the neighboring tissue, whether the tissue be bone, cartilage, or soft tissue.

In bone graft surgery, hydroxyapatite treated in accordance with this invention avoids the problems associated with autografts and allografts. Autografts offer a high fusion rate, but are commonly accompanied by complications and a high rate of morbidity at the harvesting site. Allografts offer an alternative that addresses some of these problems, but only with a significantly lower fusion rate, a high resorption rate, the potential for disease transmission, and limited availability of bone stock worldwide. Synthetic hydroxyapatite treated with both nitridation and bone morphogenetic protein can be directly substituted for the harvested bone of both autograft and allograft, avoiding many, if not all, of these problems. The surgical procedure remains otherwise the same. This invention extends to bone grafts such as those in interbody fusion procedures of the spine, as well as those in long bones.

Spinal fusions are generally used to treat injuries to the spinal vertebrae, protrusions or degeneration of the cushioning disk between vertebrae (i.e., slipped or herniated disks), abnormal curvatures of the spine, and weak or unstable spines caused by infections or tumors. The treated hydroxyapatite of this invention can also be used in the fusions and also as a cast applied against the spine for maintaining alignment of the spine, thereby replacing or supplementing internal fixation devices such as rods.

Hydroxyapatite treated in accordance with this invention can also be used in stabilizing, reinforcing, or replacing bone that has been weakened or deteriorated by metastatic deposits from tumors such as those arising from breast cancer and prostate cancer. The weakening is due to an increased rate of bone resorption caused by the deposits, and typically occurs in the spine, ribs, pelvis, and proximal long bones. Orthopedic procedures for stabilizing the weakened bones are well known and widely used. In the practice of the present invention, the treated hydroxyapatite is used in place of the conventional bone graft materials, the procedure itself being otherwise substantially the same.

The following examples are offered for illustrative purposes only.

EXAMPLE 1

This example demonstrates the synergistic effect of bone morphogenetic protein and nitridation on hydroxyapatite implants, using BMP-7 as the bone morphogenetic protein. Detection of the effect was based on the rate of bone formation at the implant site, using alkaline phosphatase (ALP) activity as an indicator of bone formation.

Pure hydroxyapatite powder was obtained from Johnson Matthey Catalog Co. (Ward Hill, Mass., USA) and nitrided by exposure to flowing dry ammonia gas at 800° C. for three hours. The nitrided powder was pressed into pellets measuring 6 mm in diameter and 2–3 mm in thickness, using an hydraulic press and a pressure of 1000 psi. The pellets were then sintered at 800° C. in flowing dry ammonia gas for ten hours, resulting in a nitrogen content of 0.88% by weight, as determined by Galbraith Laboratories (Knoxville, Tenn., USA), using the Leco method. In the Leco method, the sample is placed in a tin capsule and combusted in an oxygen atmosphere at 950° C. The combustion products are swept away with helium and gross water is removed by thermoelectric cooling. Oxygen is removed and nitrous oxides are reduced through the use of hot copper. Carbon dioxide and any remaining water are then removed and the remaining $N_2$ is measured by sweeping the gas through a thermal conductivity cell.

Additional pellets of pure, unnitrided hydroxyapatite powder were pressed and sintered in an air atmosphere at 800° C. for ten hours. The pure pellets were divided into two groups. The first group was nitrided by nitrogen ion implantation, whereby the pellets were bombarded by nitrogen ions at room temperature in two steps: 60 keV at a dose of $1.5 \times 10^{17}$ nitrogen ions per square centimeter, followed by 35 keV at a dose of $5 \times 10^{16}$ nitrogen ions per square centimeter. The ion implanted samples had a nitrogen content of 3.55±0.21 weight percent, as determined by electron microprobe analysis conducted at 10 keV using a 20 nA electron beam defocused to a diameter of 20–30 microns. The second group of pellets was left unnitrided.

The study was then performed in two halves. In the first half, pellets from each of the three groups (ammonia-nitrided, nitrided by nitrogen ion implantation, and unnitrided) were implanted in rats, with two pellets from the same group in each rat. The pellets were placed subcutaneously at bilateral sites over the pectoralis fascia. After thirteen days, the rats were sacrificed by overdose of ethyl ether, and the implants were harvested.

In the second half of the study, pellets from each of the three groups were treated with BMP-7, obtained from Creative Biomolecules, inc., of Cambridge, Mass., USA. The BMP-designated pellets were placed in a dry petri dish at room temperature (the ion-implanted pellets were placed with the ion-treated side up). Buffered saline solution (10 μL) containing 10 μg of BMPs was delivered by pipet to the center of the hydroxyapatite pellet surface and allowed to dry. These pellets were then implanted in rats in the same manner as the first half of the study, i.e., the group that did not receive the BMP-7 treatment. Three pairs of tests were thus performed, all in parallel fashion with eight pellets for each test, or a total of 48 pellets. In the first pair of tests, unnitrided pellets were used; in the second pair, pellets nitrided by ammonia treatment were used; and in the third pair, pellets nitrided by nitrogen ion implantation were used. One member of each pair had been exposed to BMP treatment while the other had not. Two rats were used in each test, for a total of 24 rats, with two identical pellets implanted in each rat.

Once the implants were harvested from the sacrificed rats, the implant sites were surveyed for immune response, and one pellet of the eight pellets from each of the six sample sets was placed in a formaldehyde-type solution for histology. The remaining seven pellets from each of the six sample sets were placed in a test tube containing 2.0 mL of a neutral saline solution to be used as the homogenization buffer in an alkaline phosphatase assay. The pellets were homogenized in the test tubes for ten seconds, using a Brinkman Polytron homogenizer at maximum speed, and the process was performed three times with a 5-second pause between each repetition. Between samples, the homogenizer was rinsed with water and any remaining tissue was removed from the blades. The homogenate was then centrifuged at 20,000×g for fifteen minutes at 4° C.

Supernatants from the centrifuged samples were then placed in test tubes. Three test tubes were prepared for each sample, one to serve as a blank and the remaining two as duplicates for the alkaline phosphatase (ALP) measurement. Prior to adding the supernatants, each tube was charged with 1.0 mL barbital buffer, 0.5 mL p-nitrophenol substrate, and 0.3 mL distilled water. The tubes designated to serve as blanks were incubated at 37° C. in a water bath for thirty minutes, then filled with 2.0 mL of 0.1 N NaOH stop solution, mixed by vortexing, and kept at room temperature. The tubes designated to serve as duplicates for the ALP measurement were simply placed in the 37° C. water bath.

The amount of supernatants added to each sample duplicate tube was 0.2 mL, except in the case of samples where high enzyme activity was anticipated, in which case only 0.05 mL of supernatant was used in order to maintain the data within the range of the spectrophotometer. Once the supernatants were added, the tubes were mixed by vortexing. After exactly thirty minutes of reaction time, the reaction in each of the ALP duplicate was stopped by adding 2.0 mL of the 0.1 N NaOH stop solution. All tubes were then equilibrated to room temperature, and optical density (OD) was read on a spectrophotometer at 410 nm for each blank and each duplicate. An average was taken of each pair of duplicates and then subtracted from the blank.

Alkaline phosphatase (ALP) activity was reported in ALP units per mg of protein. The amount of protein in each sample was determined by the Lowry Protein Assay. Additional supernatant fluid from each sample was used to measure the amount of protein present in the sample relative to known standards of bovine serum albumin (BSA), using alkaline copper solution and Folin Ciocalteau Reagent, with spectrophotometer readings at 500 nm. Protein concentrations were obtained by standard curve linear regression. The number of ALP units per mg of protein was obtained by multiplying the change in optical density by 218.58 (the average of the duplicates minus the blank) and dividing by the mg of protein per 0.2 mL aliquot of sample. The results are shown in bar graph form in FIG. 1. The vertical axis in the figure represents the ALP absorbance, and the horizontal bars represent (left to right):

(1) Hydroxyapatite pellets with no nitridation and no BMP treatment
(2) Hydroxyapatite pellets with no nitridation but having been treated with BMP-7
(3) Hydroxyapatite pellets nitrided with ammonia gas and no BMP treatment: the bar is of negligible height, indicating essentially no ALP activity
(4) Hydroxyapatite pellets nitrided with ammonia gas but having been treated with BMP-7
(5) Hydroxyapatite pellets nitrided by ion implantation and no BMP treatment: the bar is too small to be visible on the chart, indicating no ALP activity
(6) Hydroxyapatite pellets nitrided by ion implantation but having been treated with BMP-7

A comparison of bars (3) and (5) with bar (1) indicates that nitridation, whether by ammonia treatment or ion implantation, actually decreases the ALP activity. Nitridation of the implant by itself is thus detrimental to bone growth at the implant site. A comparison of bar (4) with bar (2) indicates that BMP-7 treatment when combined with nitridation produces greater ALP activity and hence greater bone growth than BMP-7 treatment alone. A comparison of bar (6) with bar (2) leads to the same conclusion, indicating that the result is consistent regardless of how nitridation is achieved. Finally, comparing bars (4) and (6) individually with the sum of bars (2) and (3) and also with the sum of bars (2) and (5) indicates that the ALP activity with the combined treatment (using either type of nitridation) achieves results that are greater than the sum of the results obtained with the individual treatments. Synergism is thus demonstrated.

The results of the immune response tests and histology studies were consistent with the alkaline phosphatase activity results.

EXAMPLE 2

This example also demonstrates the synergistic effect of bone morphogenetic protein and nitridation on hydroxyapatite implants, this time using BMP-4 as the bone morphogenetic protein. The BMP-4 protein was obtained from R & D Systems of Minneapolis, Minn., USA, and the test protocols were the same as those described above for use with BMP-7. Likewise, the same results were obtained.

The foregoing is offered primarily for purposes of illustration. Further modifications, variations, and substitutions that are still within the spirit and scope of the invention will be readily apparent to those skilled in the art.

What is claimed is:

1. A method of increasing the affinity of a hydroxyapatite component of a biomedical implant for native bone or tissue, said method comprising the following steps in any order:
   (a) nitriding the surface and a region adjacent to the surface of said hydroxyapatite component to about 1% to about 4% by weight nitridation by contacting said hydroxyapatite with a member selected from the group consisting of ammonia and ionized molecular nitrogen, and
   (b) after step (a), treating the surface of said hydroxyapatite component with a protein selected from the group consisting of BMP 2, BMP 3, BMP 4, BMP 5, BMP 6, and BMP 7.

2. A method in accordance with claim 1 in which step (b) comprises adsorbing said protein onto said surface.

3. A method in accordance with claim 1 in which said protein is BMP 4.

4. A method in accordance with claim 1 in which said protein is BMP 6.

5. A method in accordance with claim 1 in which said protein is BMP 7.

6. A biomedical implant having a hydroxyapatite component with a surface configured for contact with native bone or tissue, said biomedical implant produced by a process comprising:
   (a) nitriding the surface and a region adjacent to the surface of said hydroxyapatite component to about 1% to about 4% by weight nitridation by contacting said hydroxyapatite with a member selected from the group consisting of ammonia and ionized molecular nitrogen, and
   (b) after step (a), treating the surface of said hydroxyapatite component with a protein selected from the group consisting of BMP 2, BMP 3, BMP 4, BMP 5, BMP 6, and BMP 7.

7. A biomedical implant in accordance with claim 6 in which said protein is adsorbed onto said surface.

8. A biomedical implant in accordance with claim 6 in which said protein is BMP 4.

9. A biomedical implant in accordance with claim 6 in which said protein is BMP 6.

10. A biomedical implant in accordance with claim 6 in which said protein is BMP 7.

* * * * *